United States Patent
Deckenbach et al.

(10) Patent No.: US 9,989,411 B2
(45) Date of Patent: Jun. 5, 2018

(54) SENSOR AND METHOD FOR CHECKING AUTHENTICITY OF VALUABLE DOCUMENTS WITH A LUMINSCENT SECURITY FEATURE

(71) Applicant: GIESECKE & DEVRIENT GMBH, Munich (DE)

(72) Inventors: Wolfgang Deckenbach, Schechen (DE); Wolfgang Rauscher, Parkstetten (DE); Peter Kersten, Feldkirchen Westerham (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 291 days.

(21) Appl. No.: 14/654,033

(22) PCT Filed: Dec. 18, 2013

(86) PCT No.: PCT/EP2013/003830
§ 371 (c)(1),
(2) Date: Jun. 19, 2015

(87) PCT Pub. No.: WO2014/095055
PCT Pub. Date: Jun. 26, 2014

(65) Prior Publication Data
US 2015/0348351 A1    Dec. 3, 2015

(30) Foreign Application Priority Data
Dec. 21, 2012  (DE) ................. 10 2012 025 263

(51) Int. Cl.
*G01J 1/58*         (2006.01)
*G07D 7/00*         (2016.01)
(Continued)

(52) U.S. Cl.
CPC ............... *G01J 1/58* (2013.01); *G01N 21/64* (2013.01); *G01N 21/6408* (2013.01); *G07D 7/003* (2017.05); *G07D 7/1205* (2017.05)

(58) Field of Classification Search
CPC ............................ G07D 7/1205; G07D 7/003
See application file for complete search history.

(56) References Cited

U.S. PATENT DOCUMENTS

| | | |
|---|---|---|
| 7,067,824 B2 | 6/2006 | Muller et al. |
| 7,092,583 B2 | 8/2006 | Ahlers et al. |
| (Continued) | | |

FOREIGN PATENT DOCUMENTS

| | | |
|---|---|---|
| DE | 10113268 A1 | 9/2002 |
| DE | 10238568 A1 | 3/2004 |
| (Continued) | | |

OTHER PUBLICATIONS

German Search Report from corresponding German Application No. DE10 2012 025 263.3, dated Aug. 7, 2013.
(Continued)

*Primary Examiner* — Ajay Ojha
(74) *Attorney, Agent, or Firm* — Workman Nydegger

(57) ABSTRACT

The invention relates to a method and a sensor for checking a value document which is moved relative to the sensor. The sensor is arranged to detect the luminescence of the value document in two different spectral regions at the same location of detection simultaneously. The two temporal intensity patterns of the first and second luminescences detected in different spectral regions are evaluated relative to each other. This eliminates the motion effects which distort the two intensity patterns in the same or at least very similar manner.

13 Claims, 3 Drawing Sheets

(51) Int. Cl.
    *G07D 7/1205*     (2016.01)
    *G01N 21/64*     (2006.01)

(56) References Cited

U.S. PATENT DOCUMENTS

| | | |
|---|---|---|
| 2002/0131618 A1 | 9/2002 | Ahlers et al. |
| 2007/0145293 A1 | 6/2007 | Roth |
| 2010/0102250 A1 | 4/2010 | Li et al. |
| 2011/0147450 A1* | 6/2011 | Rapoport ............... G07D 7/122 235/375 |
| 2014/0097359 A1* | 4/2014 | Vasic ................. G01N 21/6408 250/459.1 |

FOREIGN PATENT DOCUMENTS

| | | |
|---|---|---|
| DE | 102004016249 A1 | 10/2005 |
| EP | 1237128 A1 | 9/2002 |
| FR | 2864666 A1 | 7/2005 |
| WO | 2007078949 A2 | 7/2007 |
| WO | 2012167894 A1 | 12/2012 |

OTHER PUBLICATIONS

International Search Report from corresponding PCT Application No. PCT/EP2013/003830, dated Apr. 17, 2014.
International Preliminary Report on Patentability from corresponding PCT Application No. PCT/EP2013/003830, dated Jun. 23, 2015.
Machine Translation of Russian Office Action from RU Application No. 2015 126 895, dated Jul. 9, 2017.

* cited by examiner

SENSOR AND METHOD FOR CHECKING AUTHENTICITY OF VALUABLE DOCUMENTS WITH A LUMINSCENT SECURITY FEATURE

BACKGROUND

The invention relates to a sensor and a method for checking value documents as well as to an apparatus having the sensor.

For checking value documents there are usually used sensors with which the type of the value documents is determined and/or with which the value documents are checked for authenticity and/or for their state. Such sensors are used e.g. for checking bank notes, checks, identification documents, credit cards, check cards, tickets, vouchers and the like. The value documents are checked in an apparatus for value document processing which contains one or several different sensors, depending on the value document properties to be checked. For checking the value documents, these are usually transported past the stationary sensor.

A value document to be checked may have one or several luminescent substances, of which for example the decay time of the temporal intensity pattern of the luminescence and/or spectral properties of the luminescence are checked. The luminescent substances of the value document can be present in certain regions or over the full area on the value document. For checking the decay time of the luminescence it is known to illuminate value documents with light pulses and to detect, in the dark phase between the light pulses, the luminescence intensity of the value document at different times after the end of the illumination pulse. From the temporal decay of the luminescence intensity there is then determined e.g. the decay time of the luminescence.

The disadvantage of the previous value document check is that in the case of a high transport speed of the value document there is detected a temporal intensity pattern of the luminescence, which is distorted in comparison to a statically detected intensity pattern. At high transport speeds of the value document, the decay time of the luminescence can hence be determined only inexactly.

SUMMARY

An object of the present invention is to provide a sensor for checking value documents, by which the time course of the luminescence of the value document at high transport speeds can be checked with improved accuracy.

For checking the value document, the value document is transported along a transport direction x relative to a sensor which is arranged for checking the authenticity of the value document. The value document is excited to luminesce by an excitation source, e.g. by illuminating the value document by means of an illumination device. Instead of an excitation by means of light other physical forms of excitations can also be used, however. The luminescence which the value document illuminated with the excitation light emits is detected by the sensor. In response to the luminescence excitation by the excitation source, the security feature emits a first luminescence at a first wavelength as well as a second luminescence at a second wavelength different from the first wavelength. Where applicable, further luminescences are also excited. The first luminescence has as a function of time t a first intensity pattern y1($t$) with a first characteristic time constant $\tau 1$ and the second luminescence has as a function of time t a second intensity pattern y2($t$) with a second characteristic time constant $\tau 2$. The luminescence excitation is achieved e.g. by an excitation pulse A which the excitation source directs onto the value document, cf. FIG. 2a. The first intensity pattern y1($t$) and the second intensity pattern y2($t$) then usually respectively have a building up of their luminescence intensity during the excitation pulse A of the luminescence excitation and beginning with the end of the excitation pulse of the luminescence excitation a decaying of their luminescence intensity.

The value document has a security feature which contains one or several luminescent substances which emit luminescence. Within the detection region in which the luminescence is detected, the luminescent substance emitting the first luminescence preferably has the same spatial distribution as the luminescent substance emitting the second luminescence. The luminescent substance emitting the first luminescence can be a luminescent substance different from the luminescent substance emitting the second luminescence. The first and second luminescences can also be emitted by the same luminescent substance, however. For example, this luminescent substance has several luminescent bands that are spectrally different from each other, the detected first luminescence spectrally lying within a first luminescent band of the luminescent substance and the detected second luminescence spectrally lying within a second luminescent band of the same luminescent substance.

When the first and second luminescences of the value document are detected statically, i.e. without relative motion between the value document and the sensor, the detected intensity pattern of the luminescence is not distorted by motion effects. From the statically detected intensity pattern there could then directly be ascertained the characteristic time constants of the first and second luminescences, e.g. the build-up time and/or decay time of the respective luminescence. However, in the case of a relative motion between value document and sensor the detected intensity pattern is distorted due to motion effects. One reason for this distortion is that the security feature region which is excited to luminesce is partially transported out of the (stationary) detection region while the temporal intensity pattern of the luminescence is detected.

As an example for the distorting influence of the motion, a value document 1 with a print structure 2 which has a luminescent security feature, cf. FIG. 1a, is viewed. The value document 1 is transported along a transport direction x with a transport speed v=V0≠0 relative to a detection region 3 of the value document 1 whose luminescence is detected by the sensor. For exciting the first and second luminescences, the value document is illuminated with excitation light in an illumination region which substantially matches the detection region. The illumination region could also be chosen greater or smaller than the detection region, however. In a first example it is assumed that the detection region 3 and the illumination region lie completely within the print structure 2, cf. FIG. 1a. In this case, the luminescence builds up during the excitation pulse and in case of high transport speeds is transported partially out of the detection region 3 already during the detection. Therefore, in the decaying part of the intensity pattern in the case of v=V0, there results a lower intensity than at a transport speed of v=0. Hence, the decay time which is shown by the intensity pattern detected at v=V0 is shorter than the actual decay time $\tau_1$ which would be shown by the intensity pattern at v=0, cf. FIG. 2b.

In a second example it is assumed that the detection region 3 encounters a trailing edge of the print structure 2 during the measurement in motion, cf. FIG. 1b. The detection region portion which lies behind the edge is located outside the print structure and is thus free of luminescence. In this case, moving the trailing edge through the detection region 3 leads to an even stronger decaying of the intensity pattern during the detection than in the case of v=V0 of the first example.

In a further example, the detection region 3 encounters a leading edge of the print structure 2 during the detection. This time, the detection region portion lying before the edge is located outside the print structure and is free of luminescence, cf. FIG. 1c. In this case, moving the leading edge through the detection region 3 leads to a weaker decaying of the intensity pattern than in the case of v=V0 of the first example.

A distortion by motion effects does not only occur when the security feature—like in the case of the print structure 2—is present only locally or is inhomogeneously distributed on the value document, but also when it is distributed homogeneously on the value document. An additional distortion of the detected decay time may result, when the security feature is overprinted by another printed image.

For the detection of the first and second luminescence of the security feature there is preferably used a sensor which is configured to detect the first and second luminescences of the same detection region of the value document, e.g. of the detection region 3, at the same points in time. If one now views a second luminescence of a luminescent substance which has the same spatial distribution, the intensity pattern thereof is distorted analogously to the intensity pattern of the first luminescence, cf. FIG. 2c. Hence, according to the invention, the two intensity patterns of the first and second luminescences are evaluated relative to each other. Upon the evaluation of the detected luminescence, the first and the second intensity patterns are correlated to each other. This eliminates the motion effects which distort the two intensity patterns in the same or at least very similar manner. Moreover, this relative evaluation of the intensity patterns is independent of the transport speed v of the value document.

For checking the authenticity of the value document an evaluation of the detected intensity patterns is carried out. The evaluation comprises the calculation of a first index S1 and a second index S2 with the help of a scaling-invariant function $S:R^n \rightarrow R$. For $i=1, 2 \ldots, n$, with the help of the scaling-invariant function S, the first index S1 is calculated from several first intensity values $y1(t_i)$ of the first luminescence and the second index $S2=S(y2(t_i))$ is calculated from several second intensity values $y2(t_i)$ of the second luminescence. The counter i assumes the values 1 to n, i and n being natural numbers. The detection time points $t_i$ ($i=1 \ldots, n$) lie during a building up and/or during a decaying of the first and second intensity patterns. Then the ratio V between the first index S1 and the second index S2 is determined. The ratio V is characteristic for the ratio between a first characteristic time constant $\tau 1$ of the first luminescence and a second characteristic time constant $\tau 2$ of the second luminescence. The ratio V or a value W derived from the ratio V are then used to check the authenticity of the value document.

By forming the ratio of S1 and S2 it is achieved that the motion effects which influence the detected intensity patterns of the first and second luminescences likewise are eliminated. For eliminating the motion effects it is especially advantageous that the second index S2 ($y2(t_i)$) is calculated from the second intensity values $y2(t_i)$ by the same scaling-invariant function S by which the first index S1 ($y1(t_i)$) is calculated from the first intensity values $y1(t_i)$. This achieves a precise elimination of the motion effects. On account of the scaling invariance of the function S, the two indices S1 and S2 are independent of the absolute amount of detected intensity. Hence, the indices S1 and S2 represent a relative measure for the form of the respective intensity pattern.

Moreover, it is preferred that the two indices S1 and S2 are calculated only on the basis of such intensity values of the first and second luminescences, which were detected at the same detection time points. This achieves a particularly precise elimination of the motion effects. The second intensity values $y2(t_i)$, from which the second index S2 is calculated, are detected at the same points in time $t_i$ ($i=1, 2 \ldots n$) as the first intensity values $y1(t_i)$ from which the first index S1 is calculated. The detection time points $t_i$ whose first and second intensity values are evaluated can be chosen such that they lie during the building up of the first and second intensity patterns. The detection time points $t_i$ whose first and second intensity values are evaluated can also lie during the decaying of the first and the second intensity patterns, however. It is also possible, however, that these detection time points $t_i$ are chosen to be partly during the building up and partly during the decaying of the first and the second intensity patterns.

In particular, the scaling-invariant function S has the property that the first index S1 is scaling-invariant with respect to the first intensity values $y1(t_i)$ and the second index S2 is scaling-invariant with respect to the second intensity values $y2(t_i)$. The scaling-invariant function S has for all the first intensity values $y1(t_i)$ the property $S(y1)=S(a \cdot y1)$ and for all the second intensity values $y2(t_i)$ the property $S(y2)=S(a \cdot y2)$, this property applying to any arbitrary number $a \neq 0$. The index S1 is hence a relative measure for the form of the first intensity pattern and independent of the absolute amount of the first intensity values, and the index S2 is a relative measure for the form of the second intensity pattern and independent of the absolute amount of the second intensity values.

Within the framework of the evaluation, the ratio $V=S1/S2$ is determined and the authenticity of the value document is checked on the basis of the ratio V. For the evaluation, the ratio V itself or a value derived from the ratio V, e.g. $W=V/(V+1)$ or $W=1/(V+1)$ or $W=1/V$ can be used. For example, for checking the authenticity the ratio V or the value W derived from the ratio V is compared with a reference value R which was specified for the value document or the respective sort of value document. For checking the authenticity, also a comparison with one or several thresholds can be carried out. For example, it can be checked whether V or W exceeds or undershoots a specified threshold. There can also be specified a lower threshold and an upper threshold, between which the ratio V or the value W should lie. If it is established upon the evaluation, that the ratio V or the value W lies between the upper and the lower threshold, the authenticity of the value document is affirmed. If the ratio V or the value W, however, lies above the upper or under the lower threshold, the authenticity of the value document is denied. Before this comparison, V or W is subjected to a calculation with any factor, e.g. multiplied or divided by a factor, or any offset is added or subtracted, where applicable.

The first characteristic time constant $\tau 1$ is e.g. a build-up time of the first intensity pattern and the second characteristic time constant $\tau 2$ a build-up time of the second intensity pattern. In this case, at least some of the points in time $t_i$ lie during the building up of the first and second intensity patterns. However, the first characteristic time constant $\tau 1$ can also be a decay time of the first intensity pattern and the second characteristic time constant $\tau 2$ a decay time of the second intensity pattern. In this case, at least some of the points in time $t_i$ lie during the decaying of the first and second intensity pattern.

For example, within the framework of the scaling-invariant function S the quotient $P_J/P_K$ of two linear functionals $P_J$ and $P_K$ is formed, which respectively map the first intensity values $y1(t_i)$ or second intensity values $y2(t)$, which were respectively detected at the different points in time into the space of real numbers. For calculating the first index S1, e.g. the quotient $P_J/P_K$ of two linear functionals $P_J(y1(t_i))$ and $P_K(y1(t_i))$ is formed, which respectively map several first $y1(t_i)$ intensity values detected at the different points in time $t_i$ into the space of real numbers. Also for calculating the second index S2, the quotient $P_J/P_K$ of two linear functionals $P_J(y2(t_i))$ and $P_K(y2(t_i))$ can be used, which respectively map several second $y2(t_i)$ intensity values detected at the different points in time $t_i$ into the space of real numbers. Preferably, for calculating the first index S1 there is used the quotient of the same two linear functionals $P_J$ and $P_K$ as for calculating the second index S2.

In particular, the linear functional $P_J(y1(t_j))$ maps the first intensity values $y1(t_j)$ detected at several points in time $t_j$ into the space of real numbers and the linear functional $P_K(y1(t_k))$ the first intensity values $y1(t_k)$ detected at different points in time $t_k$ into the space of real numbers, the points in time $t_k$ being different from the points in time $t_j$. For example, the counter j assumes the values $1, \ldots, (p-1)$ and the counter k the values $p \ldots, n$, where $1<p<n$ and where j, k and p are natural numbers. Analogously, the linear functional $P_J(y2(t_j))$ maps the second intensity values $y2(t_j)$ detected at several points in time $t_j$ into the space of real numbers and the linear functional $P_K(y2(t_k))$ the second intensity values $y2(t_k)$ detected at different points in time $t_k$ into the space of real numbers, the points in time $t_k$ being different from the points in time $t_j$. For example, the choice of points in time $t_k$ and the choice of points in time $t_j$ are disjoint to each other here.

For example, the points in time $t_j$ may form a continuous time period J and/or the points in time $t_k$ may form a continuous time period K. The time period J and the time period K both may lie during the building up of the first and second intensity patterns. Alternatively, the time period J and the time period K may also lie during the decaying of the first and second intensity patterns. Alternatively, one of the time periods J, K may also lie during the building up of the first and second intensity patterns and the other one of the time periods J, K during the decaying of the first and second intensity patterns. The points in time $t_j$ or $t_k$ may also lie in several non-continuous time periods J1, J2 . . . or K1, K2 . . . , which may lie in the building up and/or in the decaying of the respective intensity pattern. The points in time $t_j$ or $t_k$ may respectively also be discrete points in time which do not directly succeed one another. In particular, it is also possible to respectively use only one single point in time $t_j$ and one single point in time $t_k$ for calculating $P_J$ or $P_K$.

The linear functionals $P_J$ and $P_K$ form e.g. the sum or the integral of the first intensity values or the sum or the integral of the second intensity values, which are detected at the different points in time $t_j$ or $t_k$. When the linear functional $P_J(y1(t_j))$ is applied to the first or second intensity values $y1(t_j)$ or $y2(t_j)$, it yields e.g. the sum of the first or second intensity values of all the points in time $t_j$, i.e. $P_J(y1(t_j))=\Sigma_j(y1(t_j))$ or $P_J(y2(t_j))=\Sigma_j(y2(t_j))$. And when the linear functional $P_K(y1(t_k))$ is applied to the first or second intensity values $y1(t_k)$ or $y2(t_k)$, it yields e.g. the sum of the first or second intensity values of all the points in time $t_k$, i.e. $P_K(y1(t_k))=\Sigma_k(y1(t_k))$ or $P_K(y2(t_k))=\Sigma_k(y2(t_k))$. Instead of a sum functional the respective linear functional $P_J$ and $P_K$ may also be an evaluation functional or a derivation functional or an integral functional, however.

In the above examples, the evaluation of the luminescence of two different spectral regions was viewed. The invention is not limited to the evaluation of two spectral regions, however. Because there can also be detected and evaluated the luminescence of more than two spectral regions at the same place. For example, the luminescence at the same location of detection is simultaneously detected in four spectral regions and included in the evaluation. For each of these four spectral regions there is determined an index by means of a scaling-invariant function S. From the four indices S1, S2, S3 and S4 e.g. three ratios are formed, and an arbitrary one of these four indices is used as a reference quantity. When the index S4 is used as a reference quantity, e.g. the three ratios V1=S1/S4, V2=S2/S4 and V3=S3/S4 are determined. Instead of the ratios V1, V2, V3, there can of course also be used values W1, W2, W3 derived therefrom, which are derived from the respective ratio V1, V2, V3 analogously to the above-mentioned W. For checking the authenticity, V1, V2, V3 or W1, W2, W3 are then compared with a reference value or one or several thresholds.

For evaluating the indices S1, . . . , Sm of m different spectral regions, one can also proceed as follows: First, for each spectral region there is determined, on the basis of the function S, the respective index. From this there is determined the smallest index $S_{min}$ and the greatest index $S_{max}$ of all the m indices S1 . . . , Sm: $S_{min}$=min (S1, . . . , Sm), $S_{max}$=max (S1, . . . , Sm). $S_{min}$ is e.g. the index of the spectral region which has the fastest characteristic time constant of all the m spectral regions and $S_{max}$ is the index of the spectral region which has the slowest characteristic time constant of all the m spectral regions. Then the ratio V of the minimum index and maximum index is calculated: $V=S_{min}/S_{max}$. In this case, V states a measure for how great the time region is which is spanned by the characteristic time constants. For checking the authenticity, V or a value W derived therefrom is then compared with a reference value or one or several thresholds.

The invention also relates to a sensor for checking value documents, which is configured to carry out the method described above, in order to check the value document for authenticity. The sensor is configured for checking a value document present in a measuring plane of the sensor. The sensor is configured for detecting the intensity pattern of the first and the intensity pattern of the second luminescence of the value document as a function of time. For checking the value document, the value document is transported along the transport direction past the stationary sensor. The sensor has an evaluation device for checking the authenticity of the value document, which is configured to carry out the above-described authenticity check of the value document. For this purpose, the evaluation device has e.g. a respective programming. And the sensor has an excitation source which excites the value document to emit the first and the second luminescence. Moreover, the sensor has several photodetectors for detecting the luminescence of the value document, which the value document illuminated with the excitation light emits. The excitation of the excitation device is configured to excite a luminescence of the value document to be checked in such a way that the value document emits luminescence which is detectable by the photodetectors. The excitation source is e.g. an illumination device which illuminates the value document with excitation light. Alternatively, the excitation source can also be an electrical excitation source, so that the first and/or the second luminescence are/is an electroluminescence of the value document.

Sensors whose photodetectors detect the luminescence of the same detection region of the value document at the same point in time can be realized in different ways. For example, the sensors may have a diffraction grating or partly transmissive beam splitter in the optical structure of the detection beam path, by which different shares of the light emitted by the value document can are directed onto different photodetectors. Such sensors are known, for example, from the U.S. Pat. No. 7,067,824 B2 and from the WO2007/078949 A2.

However, in an embodiment, this is realized in the following way: The sensor has a collecting optic common to the photodetectors, through which the luminescence emitted by the value document in a detection region can be collimated to a light beam. Each of the photodetectors has associated therewith a detector lens which receives a partial light beam of the light beam collimated by the collecting optic and directs it onto the respective photodetector, so that the detection region coincides for the different photodetectors. By the sensor there can thus be detected different spectral portions of the detection light of the same detection region separately from each other at the same point in time.

The invention also relates to an apparatus for processing value documents, which has a sensor of the invention, which is configured for carrying out the above-described method. The apparatus has e.g. a transport system for transporting the value documents past the sensor along a transport direction. For example, the apparatus is a sorting apparatus for value documents.

BRIEF DESCRIPTION OF THE DRAWINGS

Hereinafter the invention will be explained by way of example with reference to the following Figures. There are shown.

DETAILED DESCRIPTION OF VARIOUS EMBODIMENTS

Figure 1A:
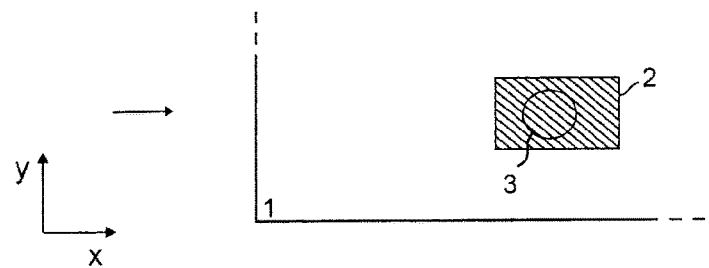
FIG. 1a-c detecting the luminescence of a luminescent print structure at three different points in time, FIG. 1d example of a sensor which is configured for the detection of the first and second luminescences at the same location of detection at the same points in time, FIG. 2a excitation pulse of the luminescence excitation, FIG. 2b-c time course of the luminescence intensity of the first and second luminescences in the case of a static check (v=0) and at a transport speed of v=V0, FIG. 3 first example of the evaluated points in time of the detected first and second intensity patterns, FIG. 4 second example of the evaluated points in time of the detected first and second intensity patterns, FIG. 5 third example of the evaluated points in time of the detected first and second intensity patterns.
Figure 1B:
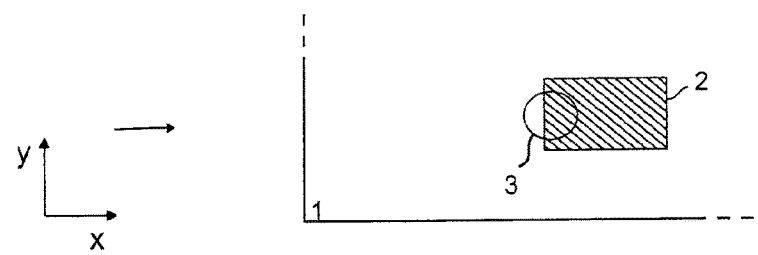

For example, the sensor is configured for checking the value document 1 in one or several measuring tracks on the respective value document 1, for each of the measuring tracks one detection device 100 being respectively provided. The sensor has a light source 20 for the luminescence excitation and at least two photodetectors 16, cf. FIG. 1d. Before each photodetector 16, viewed along the detection ray path, there is respectively disposed a detector lens 26. Like the photodetectors 16, the detector lenses 26 are also disposed side by side in one plane. To exclude a crosstalk to a different one of the detected spectral regions through scattered light, the detector lenses 26 are received separately from each other in a mount 13 of a light-non-transmissive material.

Figure 1C:
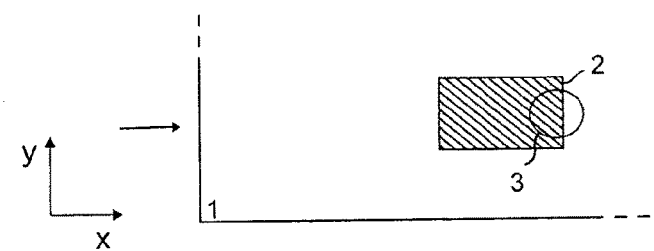
Figure 1D:
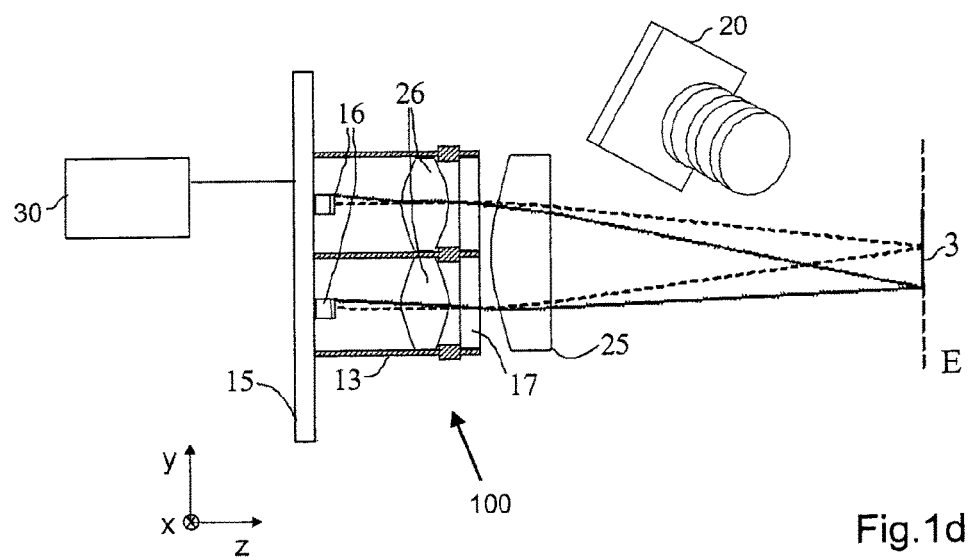

In the sectional view represented in FIG. 1c, one recognizes on the right the measuring plane E in which a value document 1 to be checked is located, and the detection region 3 of the value document, which region lies in the measuring plane E and whose luminescence is detected by the detection device 100. The luminescence light of the detection region 3 is collimated to a light beam by a collecting lens 25 common to the photodetectors 16. The photodetectors 16 and the mount 13 are fixed on a carrier 15. Viewed along the detection ray path, there is respectively disposed before each detector lens 26 a spectral filter 17. The filters 17 are transmissive to different spectral regions, so that two different spectral components of the detection light can be detected with the two photodetectors 16. The light beam is divided by the arrangement of the detector lenses 26 into partial light beams. The intermediate walls of the mount 13 serve as shielding screens between the partial light beams. In this way, the detection light of the same detection region 3 can be detected simultaneously by each of the photodetectors 16. The sensor can also detect more than two spectral components simultaneously, however, when the light beam in the detection device 100 is divided into more than two partial light beams and a respective number of further detector lenses 26 and photodetectors 16 is provided.

To detect only the luminescence of the value document, there can additionally be contained in the detection ray path a spectral edge filter which is common to all photodetectors (not shown). The spectral filters 17 are preferably interference filters which are respectively transmissive to a different spectral component of the luminescence. The photodetectors 16 are controlled such that they detect the luminescence of the detection region 3 in mutual temporal synchronism, at several detection time points $t_i$ (i=1, . . . n). In this way, the sensor can simultaneously detect the intensities of two or (if more than two photodetectors are provided) of more than two different spectral components of the detection light of the same detection region 3. Alternatively, the spectral filters 17 can also be disposed between the respective detector lens 26 and the respective photodetector 16. Or the different spectral filters can be formed by the detector lens 26 itself. Additionally or alternatively to the filters 17, the photodetectors 16 can have different spectral sensitivity. The two photodetectors 16 of FIG. 1c are disposed offset from each other perpendicularly to the transport direction x of the value document and disposed at the same position, viewed along the transport direction x. For evaluating the intensity values detected by the photodetectors 16, these are transferred to an evaluation device 30 which carries out the authenticity check of the value document 1.

Figure 3:
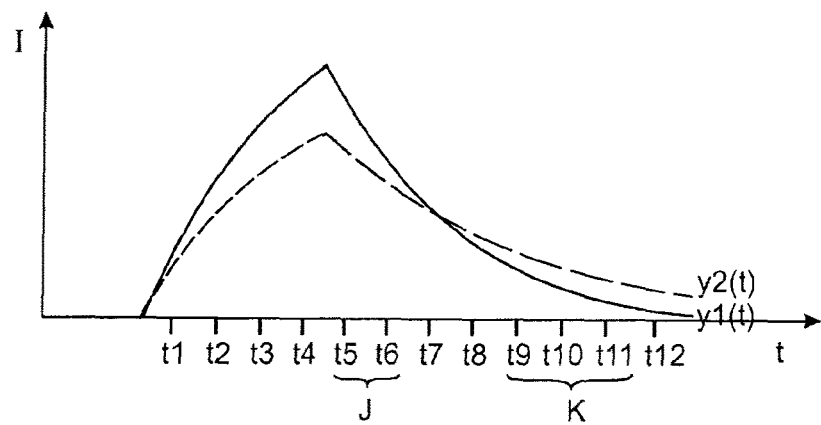

In FIG. 3 there is shown an example of the detected intensity pattern of the luminescence of a security feature of the value document 1, which the security feature emits in the case of a transport speed v=V0≠0. In the first spectral region the first intensity pattern y1(t) is detected, and in a second spectral region (spectrally deviating from the first one) the second intensity pattern y2(t) of the same security feature is detected. For the relative evaluation of the two intensity patterns, the detection time points t5 and t6 are used to calculate the linear functional $P_f$(y1(t5), y1(t6)) of the first intensity values y1(t5), y1(t6) and to calculate the linear functional $P_f$(y2(t5), y2(t6)) of the second intensity values y2(t5), y2(t6), on the one hand. On the other hand, the detection time points t9, t10 and t11 are used to calculate the linear functional $P_K(y1(t9), y1(t10), y1(t11))$ of the first intensity values $y1(t9), y1(t10), y1(t11)$ and to calculate the linear functional $P_K(y2(t9), y2(t10), y2(t11))$ of the second intensity values $y2(t9), y2(t10), y2(t11)$. For example, the linear functional $P_J$ and $P_K$ is the sum of the respective intensity values:

$$P_J(y1) = \sum_{j=5,6} y1(t_j),$$

$$P_K(y1) = \sum_{k=9,10,11} y1(t_k),$$

$$P_J(y2) = \sum_{j=5,6} y2(t_j),$$

$$P_K(y2) = \sum_{k=9,10,11} y2(t_k).$$

With the help of a scaling-invariant function $S: R^n \to R$, from the results of the two linear functionals $P_J(y1)$ and $P_K(y1)$ of the first intensity values a first index S1 is calculated. The function S forms e.g. the quotient $P_J/P_K$ of the results of the two linear functionals. The first index S1 which is characteristic for the first intensity pattern $y1(t)$ of the first luminescence, and the second index S2 which is characteristic for the second intensity pattern $y2(t)$ of the second luminescence are calculated e.g. by:

$$S1 = S(y1) = \frac{P_J(y1)}{P_K(y1)} = \frac{\sum_{j=5,6} y1(t_j)}{\sum_{k=9,10,11} y1(t_k)},$$

$$S2 = S(y2) = \frac{P_J(y2)}{P_K(y2)} = \frac{\sum_{j=5,6} y2(t_j)}{\sum_{k=9,10,11} y2(t_k)}.$$

Instead of directly using the quotient $P_J/P_K$ of the added intensity values $y1(t)$ or $y2(t)$, the function S may also comprise that the intensity values $y1(t), y2(t)$ are first multiplied with a factor.

The two calculated indices S1 and S2 are then correlated to each other. For evaluating, e.g. their ratio V=S1/S2 is used. In this case, the ratio V is determined by $$V = \frac{S_1}{S_2} = \frac{\sum_{j=5,6} y1(t_j) / \sum_{k=9,10,11} y1(t_k)}{\sum_{j=5,6} y2(t_j) / \sum_{k=9,10,11} y2(t_k)}.$$

Figure 2A:
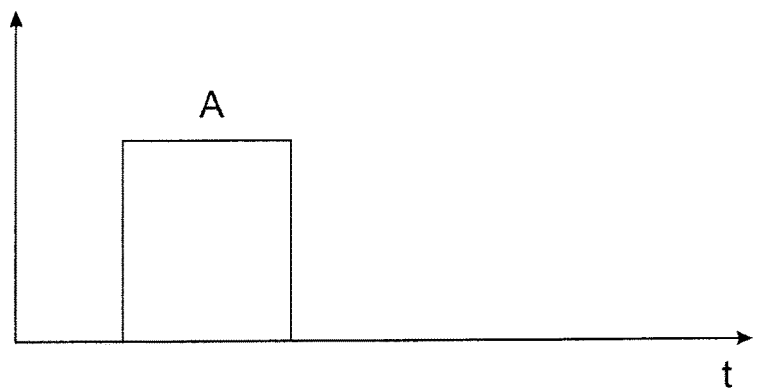
Figure 2B:
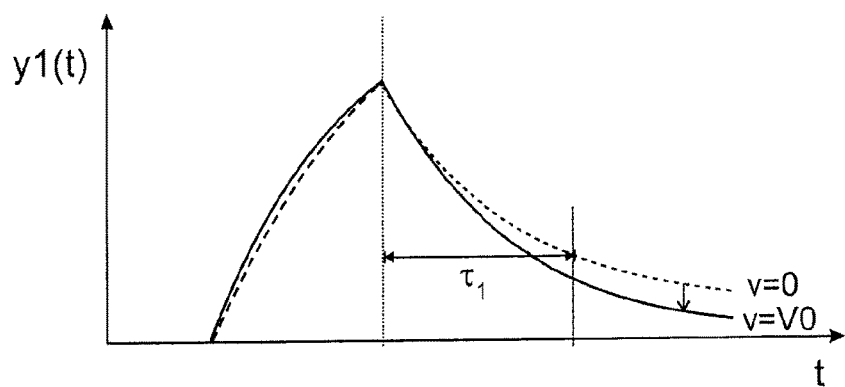
Figure 2C:
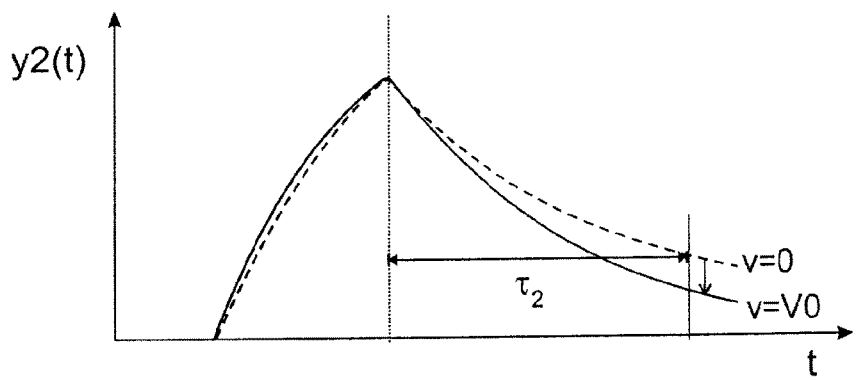

By the formation of the ratio, disturbing influences which are caused by the motion of the value document and which have distorted the detected luminescent courses $y1(t)$ and $y2(t)$ are largely eliminated. In the example of FIG. 3, the ratio V is thus characteristic for the ratio between the actual decay time $\tau_1$ of the first luminescence and the actual decay time $\tau_2$ of the second luminescence, cf. FIG. 2b, 2c.

Instead of forming the quotient $P_J/P_K$, a different scaling-invariant function S can be used for the calculation of the two indices S1 and S2, however. If one uses, for example, for $P_J$ a derivation functional and for $P_K$ a sum functional, one obtains for the ratio V:

$$V = \frac{S_1}{S_2} = \frac{(y1(t_6) - y1(t_5)) / \left((t_6 - t_5) \cdot \sum_{k=9,10,11} y1(t_k)\right)}{(y2(t_6) - y2(t_5)) / \left((t_6 - t_5) \cdot \sum_{k=9,10,11} y2(t_k)\right)}.$$

By the evaluation with the help of a scaling-invariant function S it is achieved that disturbances or defects of the measuring system, which influence the absolute values of the detected intensities, do not affect the evaluation.

Figure 4:
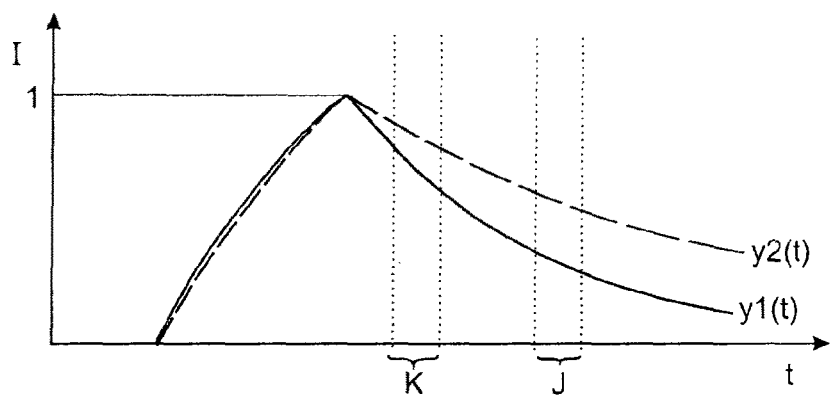

In FIG. 4, there is represented a second example with different points in time $t_j$ and $t_k$ to be evaluated. In this example, instead of individual discrete points in time, intensity values $y1(t)$ and $y2(t)$ detected virtually continuously are evaluated. Virtually continuously here means that not only individual, but in each case a plurality of intensity values detected shortly one after the other are used during a certain time interval. For calculating $P_J$ of the first luminescence, the intensity values $y1(t)$ (normalized to 1) are used, which are detected in the first spectral region during the time period J, and for calculating $P_J$ of the second luminescence, the intensity values $y2(t)$ (normalized to 1) are used, which are detected in the second spectral region during the time period J. For calculating $P_K$, the respective intensity values $y1(t)$ or $y2(t)$ are used, which are detected during the time period K, cf. FIG. 4. The two indices S1 and S2 are then calculated as follows:

$$S2 = \frac{P_J(y2)}{P_K(y2)} = \frac{\int_J y2(t)dt}{\int_K y2(t)dt}.$$

If one assumes, that the time period K begins 50 μs after the end of the excitation, the duration of the time period K and J in each case amounts to 50 μs, and their temporal distance is 100 μs, in the case of the example of FIG. 4 there results for the indices S1 and S2 the numerical values S1≈16/34≈0.47 and S2≈29/41≈0.70. From S1 and S2 there can then be formed, on the basis of the ratio V=S1/S2, e.g. the value W=V/(V+1) derived from V. In the example of the FIG. 4, there results W=S1/(S1+S2)≈0.40. The value W derived from V is characteristic for the ratio between the (actual) decay time $\tau_1$ of the first luminescence $y1(t)$ and the (actual) decay time $\tau_2$ of the second luminescence $y2(t)$. In general, W<0.5 applies, if the decay time $\tau_1$ of the first luminescence $y1(t)$ is smaller than the decay time $\tau_2$ the second luminescence $y2(t)$. Vice versa, W>0.5 applies, if the decay time $\tau_1$ of the first luminescence $y1(t)$ is larger than the decay time $\tau_2$ of the second luminescence $y2(t)$. And W=0.5 applies, if the decay times of the first luminescence and of the second luminescence $y2(t)$ are the same.

For the security feature, from which the intensity patterns shown in Figure to 4 were detected, it was possible to establish before the authenticity check that without motion effects (e.g. ascertainable by a static measurement), i.e. at v=0, it has in the first spectral region a decay time of the first luminescence $y1(t)$ of $\tau_1$=200 μs and in the second spectral region a decay time of the second luminescence $y2(t)$ of $\tau_2$=400 μs. On the basis of these undistorted decay times there can be defined a reference value R for the value W obtained upon the evaluation. Within the framework of the authenticity check of the value document, the ascertained value W can then be compared with this reference value R. If upon the comparison there results a deviation between W and the reference value R which is too great, the authenticity of the value document is denied.

Figure 5:
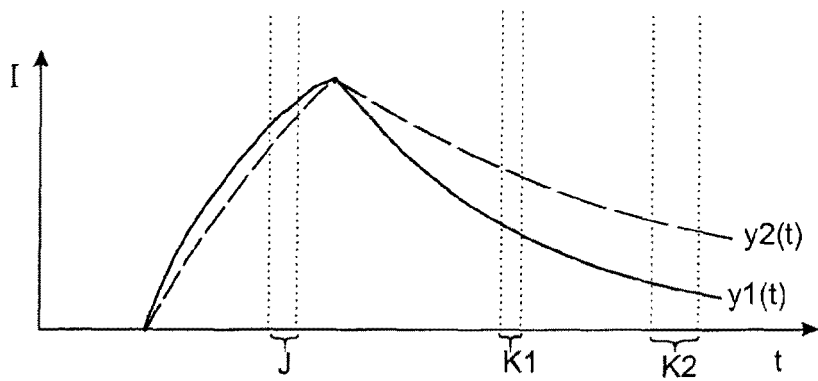

In FIG. 5 there is represented a third example, in which for the evaluation there are used points in time $t_j$ and $t_k$ during as well as after the excitation. Also in this example, virtually continuously detected intensity values y1(t) and y2(t) are evaluated. For calculating $P_J$ of the first or second luminescences, the intensity values y1(t) or y2(t) are used which are detected during the time period J in the building up part of the respective intensity pattern y1(t) and y2(t). In this example, for calculating $P_K$, the respective intensity values of two mutually separate time periods K1 and K2, which lie in the decaying part of the respective intensity pattern, are added up. The two indices S1 and S2 are then calculated as follows:

$$S1 = \frac{P_J(y1)}{P_K(y1)} = \frac{\int_J y1(t)dt}{\int_{K1} y1(t)dt + \int_{K2} y1(t)dt},$$

$$S2 = \frac{P_J(y2)}{P_K(y2)} = \frac{\int_J y2(t)dt}{\int_{K1} y2(t)dt + \int_{K2} y2(t)dt}.$$

From S1 and S2 again a ratio V=S1/S2 is formed. Since in this example there are evaluated intensity values which were detected during the building up of the luminescence as well as those which were detected during the decaying of the luminescence, the ratio V is characteristic for the decay time as well as for the build-up time of the first luminescence and the second luminescence.

The invention claimed is:

1. A method for checking the authenticity of value documents which for checking their authenticity are transported past a sensor and which have a security feature which in response to a luminescence excitation by an excitation source emits a first luminescence at a first wavelength, which has as a function of time t a first intensity pattern y1(t) with a first characteristic time constant τ1, as well as a second luminescence at a second wavelength different from the first wavelength, which has as a function of time t a second intensity pattern y2(t) with a second characteristic time constant τ2, with the following steps:
   detecting the first intensity pattern y1(t) and the second intensity pattern y2(t) as a function of time t at the same location of detection of the security feature with the help of the sensor;
   calculating a first index S1=S(y1($t_i$)), with i=1, 2, . . . , n, with the help of a scaling-invariant function S:R$^n$→R from several first intensity values y1($t_i$) of the first luminescence, which are detected at different points in time $t_i$ during a building up and/or during a decaying of the first identity pattern y1(t);
   calculating a second index S2=S(y2($t_i$)), with i=1, 2 . . . , n, with the help of a scaling-invariant function S:R$^n$→R from several second intensity values y2($t_i$) of the second luminescence, which are detected at the different points in time $t_i$ during a building up and/or during a decaying of the second intensity pattern y2($t_i$);
   determining a ratio V between the first index S1 and the second index S2; and
   checking the authenticity of the value document on the basis of the ratio V or on the basis of a value W derived from the ratio V, wherein the scaling-invariant function S has the property that the first index S1 is scaling-invariant with respect to the first intensity values y1($t_i$) and the second index S2 is scaling-invariant with respect to the second intensity values y2($t_i$).

2. The method according to claim 1, wherein for the calculation of the first index S1 and of the second index S2 the same scaling-invariant function S is used.

3. The method according to claim 1, wherein at least some of the points in time $t_i$ lie during the building up of the first and second intensity patterns and the ratio V is a measure for the ratio between the build-up time of the first intensity pattern y1(t) and the build-up time of the second intensity pattern y2(t).

4. The method according to claim 1, wherein at least some of the points in time $t_i$ lie during the decaying of the first and second intensity patterns and the ratio V is a measure for the ratio between the decay time of the first intensity pattern y1(t) and the decay time of the second intensity pattern y2(t).

5. The method according to claim 1, wherein the second intensity values y2($t_i$), from which the second index S2 is calculated, for i=1, 2 . . . , n, are detected at the same points in time $t_i$ as the first intensity values y1($t_i$), from which the first index S1 is calculated.

6. The method according to claim 1, wherein within the framework of the scaling-invariant function S there is formed the quotient $P_J/P_K$ of two different linear functionals $P_J$ and $P_K$, which respectively map the first intensity values y1($t_i$) or second intensity values y2($t_i$) detected at the different points in time $t_i$ into the space of real numbers.

7. The method according to claim 1, wherein for the calculation of the first index S1, the quotient $P_J$(y1($t_i$))/$P_K$(y1($t_i$)) of two different linear functionals $P_J$(y1($t_i$)) and $P_K$(y1($t_i$)) is used, which respectively map several first y1($t_i$) intensity values detected at the different points in time $t_i$ into the space of real numbers, and that for the calculation of the second index S2, the quotient $P_J$(y2($t_i$))/$P_K$(y2($t_i$)) of two different linear functionals $P_J$(y2($t_i$)) and $P_K$(y2($t_i$)) is used, which respectively map several second intensity values y2($t_i$) detected at the different points in time $t_i$ into the space of real numbers.

8. The method according to claim 1, wherein for the calculation of the first index S1 there is used the same linear functional $P_J$ and the same linear functional $P_K$ as for the calculation of the second index S2, wherein for the first index S1 the linear functionals $P_J$ and $P_K$ are calculated on the basis of the first intensity values y1($t_i$) and wherein for the second index S2 the linear functionals $P_J$ and $P_K$ are calculated on the basis of the second intensity values y2($t_i$).

9. The method according to claim 1, wherein the linear functional $P_J$(y1($t_i$)) maps the first intensity values y1($t_j$) detected at several points in time $t_j$ into the space of real numbers and that the linear functional $P_K$(y1($t_i$)) maps the first intensity values y1($t_k$) detected at several points in time $t_k$ into the space of real numbers and that the linear functional $P_J$(y2($t_i$)) maps the second intensity values y2($t_j$) detected at several points in time $t_j$ into the space of real numbers and that the linear functional $P_K$(y2($t_i$)) maps the second intensity values y2($t_k$) detected at several points in time $t_k$ into the space of real numbers, wherein the points in time $t_k$ are different from the points in time $t_j$.

10. The method according claim 1, wherein by the linear functional $P_J$, applied to the first intensity values y1($t_j$), there is calculated an integral or a sum of the first intensity values y1($t_j$), and that by the linear functional $P_J$, applied to the second intensity values y2($t_j$), there is calculated an integral or a sum of the second intensity values y2($t_j$), and that by the linear functional $P_K$, applied to the first intensity values $y1(t_k)$, there is calculated an integral or a sum of the first intensity values $y1(t_k)$, and that by the linear functional $P_K$, applied to the second intensity values $y2(t_k)$, there is calculated an integral or a sum of the second intensity values $y2(t_k)$, wherein the points in time $t_k$ are different from the points in time $t_j$.

11. A sensor for checking value documents which for their check are transported along a transport direction (x) past the sensor, the value documents having a security feature which in response to a luminescence excitation by an excitation source emits a first luminescence at a first wavelength, which has as a function of time t a first intensity pattern $y1(t)$ with a first characteristic time constant $\tau 1$, as well as a second luminescence at a second wavelength different from the first wavelength, which has as a function of time t a second intensity pattern $y2(t)$ with a second characteristic time constant $\tau 2$, the sensor comprising:

an excitation source for exciting a first luminescence and a second luminescence of the value document;

at least two photodetectors for detecting the first and second luminescence which the value document excited by the excitation source emits in a detection region, wherein the luminescence of the value document is detectable by the photodetectors in at least two different spectral regions and wherein the sensor is configured such that the photodetectors respectively detect the luminescence of the same detection region of the value document at the same points in time; and an evaluation device which is configured to carry out an authenticity check of the value documents by detecting the first intensity pattern $y1(t)$ and the second intensity pattern $y2(t)$ as a function of time t at the same location of detection of the security feature with the help of the sensor, calculating a first index $S1=S(y1(t_i))$, with $i=1, 2, \ldots, n$, with the help of a scaling-invariant function $S:R^n \to R$ from several first intensity values $y1(t_i)$ of the first luminescence, which are detected at different points in time $t_i$ during a building up and/or during a decaying of the first identity pattern $y1(t)$, calculating a second index $S2=S(y2(t_i))$, with $i=1, 2 \ldots, n$, with the help of a scaling-invariant function $S:R^n \to R$ from several second intensity values $y2(t_i)$ of the second luminescence, which are detected at the different points in time $t_i$ during a building up and/or during a decaying of the second intensity pattern $y2(t_i)$, determining a ratio V between the first index S1 and the second index S2, and checking the authenticity of the value document on the basis of the ratio V or on the basis of a value W derived from the ratio V, wherein the scaling-invariant function S has the property that the first index S1 is scaling-invariant with respect to the first intensity values $y1(t_i)$ and the second index S2 is scaling-invariant with respect to the second intensity values $y2(t_i)$.

12. An apparatus for checking value documents with a sensor according to claim 11.

13. A sensor for checking value documents which for their check are transported along a transport direction (x) past the sensor, the value documents having a security feature which in response to a luminescence excitation by an excitation source emits a first luminescence at a first wavelength, which has as a function of time t a first intensity pattern $y1(t)$ with a first characteristic time constant $\tau 1$, as well as a second luminescence at a second wavelength different from the first wavelength, which has as a function of time t a second intensity pattern $y2(t)$ with a second characteristic time constant $\tau 2$, the sensor comprising:

an excitation source for exciting a first luminescence and a second luminescence of the value document;

at least two photodetectors for detecting the first and second luminescence which the value document excited by the excitation source emits in a detection region, wherein the luminescence of the value document is detectable by the photodetectors in at least two different spectral regions and wherein the sensor is configured such that the photodetectors respectively detect the luminescence of the same detection region of the value document; and an evaluation device which is configured to carry out an authenticity check of the value documents by detecting the first intensity pattern $y1(t)$ and the second intensity pattern $y2(t)$ as a function of time t at the same location of detection of the security feature with the help of the sensor, calculating a first index $S1=S(y1(t_i))$, with $i=1, 2, \ldots, n$, with the help of a scaling-invariant function $S:R^n \to R$ from several first intensity values $y1(t_i)$ of the first luminescence, which are detected at different points in time $t_i$ during a building up and/or during a decaying of the first identity pattern $y1(t)$, calculating a second index $S2=S(y2(t_i))$, with $i=1, 2 \ldots, n$, with the help of a scaling-invariant function $S:R^n \to R$ from several second intensity values $y2(t_i)$ of the second luminescence, which are detected at the different points in time $t_i$ during a building up and/or during a decaying of the second intensity pattern $y2(t_i)$, determining a ratio V between the first index S1 and the second index S2, and checking the authenticity of the value document on the basis of the ratio V or on the basis of a value W derived from the ratio V, wherein the scaling-invariant function S has the property that the first index S1 is scaling-invariant with respect to the first intensity values $y1(t_i)$ and the second index S2 is scaling-invariant with respect to the second intensity values $y2(t_i)$.

* * * * *